(12) United States Patent
Jacob et al.

(10) Patent No.: US 8,766,790 B2
(45) Date of Patent: Jul. 1, 2014

(54) WIRELESS IDENTIFICATION OF A COMPONENT OF A PRESSURE SUPPORT SYSTEM

(75) Inventors: Lawrence Anthony Jacob, Sewickley, PA (US); John Raymond Pujol, Murrysville, PA (US); Benjamin Irwin Shelly, Pittsburgh, PA (US); David W. Smith, Oakmont, PA (US); Richard Andrew Sofranko, Finleyville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 230 days.

(21) Appl. No.: 13/509,307

(22) PCT Filed: Oct. 15, 2010

(86) PCT No.: PCT/IB2010/054684
§ 371 (c)(1),
(2), (4) Date: May 11, 2012

(87) PCT Pub. No.: WO2011/058462
PCT Pub. Date: May 19, 2011

(65) Prior Publication Data
US 2012/0229272 A1 Sep. 13, 2012

Related U.S. Application Data

(60) Provisional application No. 61/260,033, filed on Nov. 11, 2009.

(51) Int. Cl.
*G08B 1/08* (2006.01)
*A61M 16/00* (2006.01)
*A61M 16/06* (2006.01)
*A61M 15/00* (2006.01)
*A61B 5/00* (2006.01)

(52) U.S. Cl.
CPC ............... *A61M 16/00* (2013.01); *A61M 16/06* (2013.01); *A61M 15/00* (2013.01); *A61B 5/0031* (2013.01)
USPC ................................ 340/539.12; 128/200.24

(58) Field of Classification Search
CPC ..... A61M 16/00; A61M 16/06; A61M 15/00; A61B 5/0031
USPC ..................................................... 340/539.12
See application file for complete search history.

(56) References Cited

U.S. PATENT DOCUMENTS

| 660,568 A | 10/1900 | Gathmann |
| 3,958,558 A | 5/1976 | Dunphy |

(Continued)

FOREIGN PATENT DOCUMENTS

| WO | 2007140512 A1 | 12/2007 |
| WO | WO2008091164 A1 | 7/2008 |

*Primary Examiner* — Kerri McNally
(74) *Attorney, Agent, or Firm* — Michael W. Haas

(57) ABSTRACT

An airway pressure support system (2) that includes a pressure generating device (4) structured to produce a flow of gas and a component (8) such as a patient interface device (8) structured to be selectively coupled to the pressure generating device (4), wherein the pressure generating device (4) and the component (8) are structured to enable the component (8) to be to wirelessly identified by the pressure generating device (4) only when the component (8) is coupled to the pressure generating device (4). Also, a method of identifying a component (8) in an airway pressure support system (2) that includes steps of coupling the component (8) to a pressure generating device (4) of the airway pressure support system (2) and enabling the component (8) to be to wirelessly identified by the pressure generating device (4) only when the component (8) is coupled to the pressure generating device.

22 Claims, 9 Drawing Sheets

(56) References Cited

U.S. PATENT DOCUMENTS

| | | |
|---|---|---|
| 4,206,721 A | 6/1980 | Lee |
| 4,206,762 A | 6/1980 | Cosman |
| 4,281,666 A | 8/1981 | Cosman |
| 4,281,667 A | 8/1981 | Cosman |
| 4,385,636 A | 5/1983 | Cosman |
| 4,653,508 A | 3/1987 | Cosman |
| 4,938,068 A | 7/1990 | Clements |
| 5,058,588 A | 10/1991 | Kaestle |
| 5,115,675 A | 5/1992 | Feldman |
| 5,191,317 A | 3/1993 | Toth |
| 5,339,051 A | 8/1994 | Koehler |
| 5,551,419 A | 9/1996 | Froehlich |
| 5,813,280 A | 9/1998 | Johnson |
| 6,111,520 A | 8/2000 | Allen |
| 6,113,553 A | 9/2000 | Chubbuck |
| 6,461,301 B2 | 10/2002 | Smith |
| 7,082,835 B2 | 8/2006 | Cook |
| 8,210,178 B2 * | 7/2012 | Schermeier et al. ..... 128/205.28 |
| 2005/0268916 A1 | 12/2005 | Mumford |
| 2006/0117859 A1 | 6/2006 | Liu |
| 2007/0251527 A1 | 11/2007 | Sleeper |
| 2007/0272240 A1 | 11/2007 | Aylsworth |
| 2007/0277824 A1 * | 12/2007 | Aylsworth et al. ....... 128/204.23 |
| 2008/0264413 A1 | 10/2008 | Doherty |
| 2009/0025728 A1 | 1/2009 | Aljuri |

* cited by examiner

WIRELESS IDENTIFICATION OF A COMPONENT OF A PRESSURE SUPPORT SYSTEM

CROSS-REFERENCE TO RELATED APPLICATIONS

This patent application claims the priority benefit under 35 U.S.C. §119(e) of U.S. Provisional Application No. 61/260,033 filed on Nov. 11, 2009, the contents of which are herein incorporated by reference.

BACKGROUND OF THE INVENTION

1. Field of the Disclosure

The present invention relates to pressure support systems, and, more particularly, to a pressure support system in which a component of the system, such as, without limitation, a patient interface device, may be wirelessly identified by the system.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a respiratory patient interface device, including a mask component, on the face of a patient. The mask component may be, without limitation, a nasal mask that covers the patient's nose, a nasal cushion having nasal prongs that are received within the patient's nares, a nasal/oral mask that covers the nose and mouth, or full face mask that covers the patient's face. The respiratory patient interface device interfaces the ventilator or pressure support device with the airway of the patient so that a flow of breathing gas can be delivered from the pressure/flow generating device to the airway of the patient.

It is common for users of pressure support devices to have several different patient interface devices (e.g., different masks and different patient interface components), tubing options, or other component options (such as bacteria filters) that they use for reasons such as comfort. It is important for the pressure support device to know which type of patient interface device or other component is being used so that it will know certain information about the components, such as, without limitation, mask resistance, mask compliance, mask leak rates. Based on this information, the pressure support device can adjust the operating parameters of the unit. In addition, certain comfort features or device functions can be enabled on the basis of a particular mask or peripheral being attached.

Current systems allow for patient interface device detection in a number of different ways. In some systems, a user can manually key the patient interface device type into the system. Another solution that has been suggested is to identify the patient interface deice using RFID technology. This works well, but does not address the scenario where there are multiple patient interface devices in the same room. In such as case, the RFID reader would likely detect all of the patient interface devices in the room, rather than a selected one of the devices.

SUMMARY OF THE INVENTION

Accordingly, it is an object of the present invention to provide a pressures support system that overcomes the shortcomings of conventional systems. This object is achieved according to one embodiment of the present invention by providing a pressure support system that includes a pressure generating device structured to produce a flow of gas and a component, such as patient interface device, structured to be selectively coupled to the pressure generating device, wherein the component and the patient interface device are structured to enable the component to be to wirelessly identified by the pressure generating device only when the component is coupled to the pressure generating device.

In another embodiment, a method of identifying a component, such as a patient interface device, in a pressure support system is provided that includes steps of coupling the component to a pressure generating device of the airway pressure support system and enabling the component to be to wirelessly identified by the pressure generating device only when the component is coupled to the pressure generating device.

In another particular embodiment, a pressure support system is provided that includes a pressure generating device structured to produce a flow of gas, the pressure generating device having an optical emitter structured to emit broadband light and an optical detector, a delivery conduit operatively coupled to the pressure generating device, the delivery conduit having a first light transmitting element operatively coupled to the optical emitter and a second light transmitting element operatively coupled to the optical detector, and a patient interface device structured to be selectively coupled to the delivery conduit. The patient interface device has an optical filter structured to be operatively coupled to the first light transmitting element and the second light transmitting element when the patient interface device is coupled to the delivery conduit. The optical filter is structured to receive the broadband light from the optical emitter through the first light transmitting element and in response thereto output filtered light of a specific frequency or range of frequencies that is associated with the patient interface device. The filtered light is transmitted to the optical detector through the second light transmitting element, the optical detector being structured to detect the specific frequency or range of frequencies. The system further includes a controller operatively coupled to the optical detector that is programmed to identify the patient interface device based on the detected specific frequency or range of frequencies.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Figure 1:
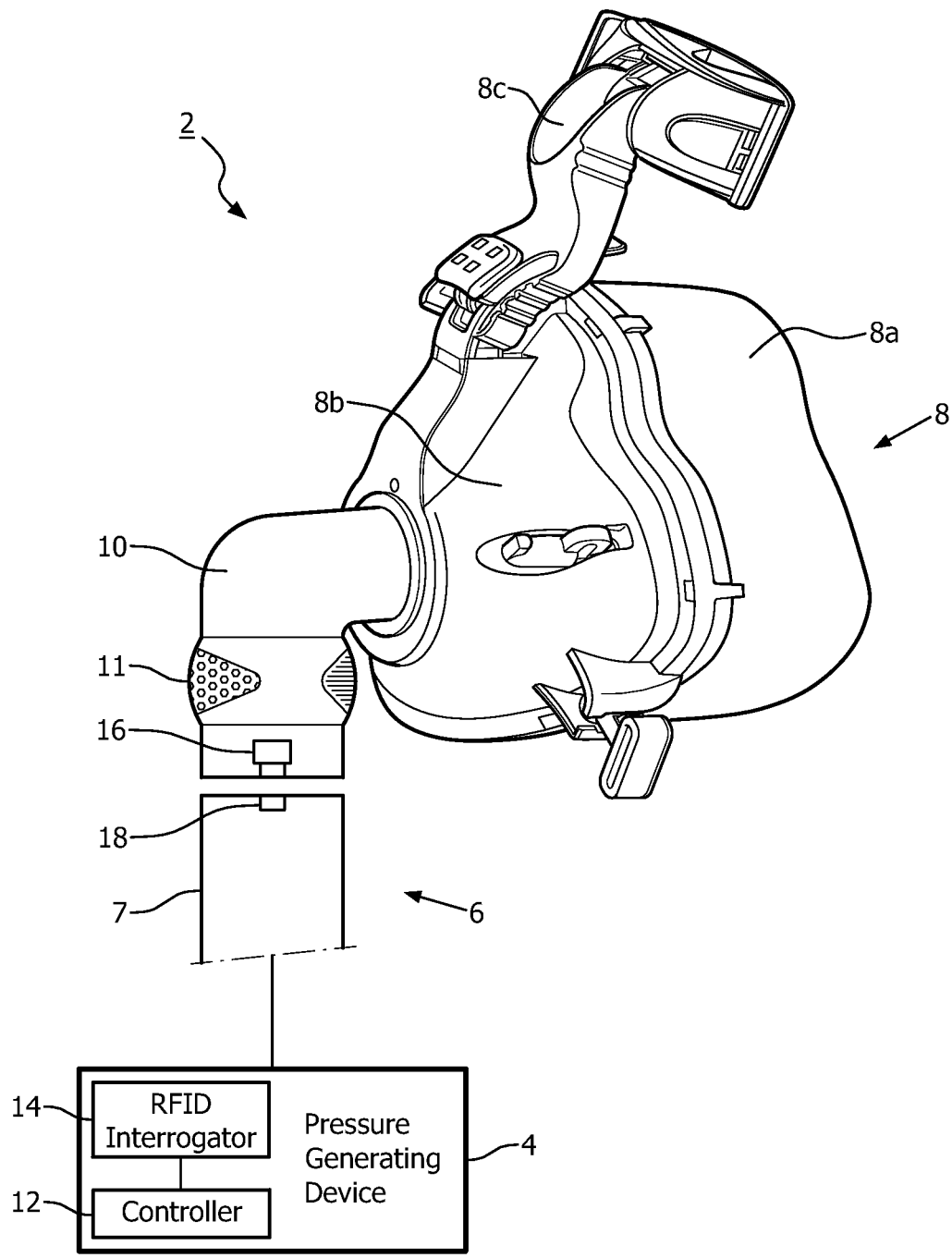
FIG. 1 is a schematic diagram of a pressure support system adapted to provide a regimen of respiratory therapy to a patient according to one embodiment.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. As employed, herein, the statement that two or more parts or components are "coupled" together shall mean that the parts are joined or operate together either directly or through one or more intermediate parts or components. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

The present invention provides in the various embodiments described herein provides an airway pressure support system in which a component of the system may be wirelessly identified by the system wherein such wireless identification is enabled only if the component is operatively coupled to the system.

A pressure support system 2 adapted to provide a regimen of respiratory therapy to a patient according to one embodiment is generally shown in FIG. 1. System 2 includes a pressure generating device 4 and a patient circuit 6 including a delivery conduit 7 and a patient interface device 8. Although system 2 is discussed as including pressure generating device 4, patient circuit 6, and patient interface device 8 as shown, it is contemplated that other systems may be employed while remaining within the scope of the present invention. For example, and without limitation, a system in which the pressure generating device is coupled to a patient interface device having exhaust port assembly integrated therein is contemplated.

Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Respironics, Inc. of Murrysville, Pa.), and auto-titration pressure support devices. As seen in FIG. 1, pressure generating device 4 includes a controller 12, which may be, for example, a microprocessor, a microcontroller or some other suitable processing device, that includes or is operatively coupled to a memory (not shown) that provides a storage medium for data and software executable by controller 12 for controlling the operation of pressure generating device 4 and airway pressure support system 2.

Pressure generating device 4 includes an RFID interrogator 14 (sometimes also referred to as an RFID reader) operatively coupled to controller 12. Alternatively, part or all of RFID interrogator 14 and its functionality may be part of controller 12. RFID interrogator 14 is structured to be able to communicate with RFID tags over an air interface by way of RF signals, and in particular to query the RFID tags for information stored on them, which can be, for example, identification information. The purpose and functionality of RFID interrogator 14 in airway pressure support system 2 is described in detail elsewhere herein.

Delivery conduit 7 is structured to communicate the flow of breathing gas from pressure generating device 4 to patient interface device 8. Typically, delivery conduit 7 includes one or more individual conduits or tubes, a first end of which couples with pressure generating device 4 and a second end of which couples with patient interface device 8. In the current embodiment, the second end is coupled with patient interface device 8 through a fluid coupling device 10 of patient interface device 8.

Patient interface device 8 is typically a nasal or nasal/oral mask structured to be placed on and/or over the face of a patient. Any type of patient interface device 8, however, which facilitates the delivery of the flow of breathing gas to, and the removal of a flow of exhalation gas from, the airway of such a patient may be used while remaining within the scope of the present invention. In the embodiment shown in FIG. 1, patient interface device 8 includes a cushion 8a, a rigid shell 8b, and a forehead support 8c. Straps (not shown) may be attached to shell 8b and/or forehead support 8c to secure patient interface device 8 to the patient's head. In addition, patient interface device 8 in the exemplary illustrated embodiment includes a fluid coupling device 10 (e.g., an elbow connector as shown) having exhaust port assembly 11. It is to be understood that the present invention contemplates that patient interface device 8 can have any configuration and can be any one of a number of different patient interface devices, such as a nasal mask, nasal cannula, full face (i.e., nasal and oral) mask. Also, fluid coupling device 10 can be any suitable coupling having any suitable configuration or it can be omitted entirely with the RFID components discussed below being provided on another portion of the mask to which delivery conduit 7 connects.

An opening in shell 8b, to which fluid coupling device 10 is coupled, allows the flow of breathing gas from pressure generator device 4 to be communicated to an interior space defined by shell 8b and cushion 8a, and then, to the airway of a patient. The opening in shell 8b also allows the flow of exhalation gas (from the airway of such a patient) to be communicated to exhaust port assembly 11 in the current embodiment.

As seen in FIG. 1, fluid coupling device 10 of patient interface device 8 is provided with and supports an RFID component 16 and the second end of delivery conduit 7 is provided with and supports a coupling component 18. RFID component 16 includes an RFID integrated circuit (IC) chip 20 (FIGS. 2 and 3), and, depending on the particular embodiment, may include all or part of an antenna that allows IC chip 20 to communicate with RFID interrogator 14. IC chip 20 stores information that identifies patient interface device 8 to pressure generating device 4 (e.g., by type or style), and may include further information that provides one or more operating parameters for pressure generating device 4 to be associated with patient interface device 8.

According to an aspect of the present embodiment, RFID component 16 is structured so that it is not fully functional, meaning it does not enable IC chip 20 to communicate with RFID interrogator 14 (e.g. when polled by RFID interrogator 14) unless and until patient interface device 8 is coupled to delivery conduit 7. In addition, in the present embodiment, RFID component 16 is structured to become fully functional when patient interface device 8 is coupled to delivery conduit 7 due to the presence of coupling component 18 and its cooperation with RFID component 16. A number of particular embodiments of RFID component 16 and coupling component 18 are described below. In addition, while RFID component 16 is in the illustrated embodiment(s) shown as being provided in fluid coupling device 10, it may be provided in other parts of patient interface device 8, such as, without limitation, shell 8b.

In operation, when patient interface device 8 is coupled to delivery conduit 7, RFID component 16 will become fully functional as just described, and, in essence, RFID component 16 and coupling component 18 will together form a complete RFID tag. Thereafter, RFID interrogator 14 may send an RF interrogation/polling signal to RFID component 16 which will cause IC chip 20 to transmit via RF the information stored therein. As a result, pressure generating device 4 will be able to identify patient interface device 8 and control operation based on the information that is received. In addition, as will be appreciated, any other similarly structured patient interface devices 8 that may be within range of RFID interrogator 14 (e.g., in the same room) will have RFID components 16 that are not fully functional because the patient interface device 8 is not coupled to delivery conduit 7. Therefore, IC chip 20 in those devices will not send any information to pressure generating device 4 in response to the interrogation/polling signal. Thus, in short, in the present embodiment, pressure generating device 4 will detect only the patient interface device 8 that is coupled to it and being used by the patient and all other patient interface devices 8 in the vicinity will be unrecognizable. This allows a patient to seamlessly change patient interface devices 8 without requiring the patient to perform any additional steps like keying the mask type into pressure generating device 4 and/or changing operating parameters on pressure generating device 4. This would be highly beneficial in an environment multiple patient interface devices 8 are typically present, such as a sleep lab.

RFID component 16 and coupling component 18 together may take on the form of either a passive RFID tag, which does not have an internal power supply is power by the incoming RF signal from RFID interrogator 14, or an active RFID tag, which does have its own internal power supply such as a battery.

Figure 2:
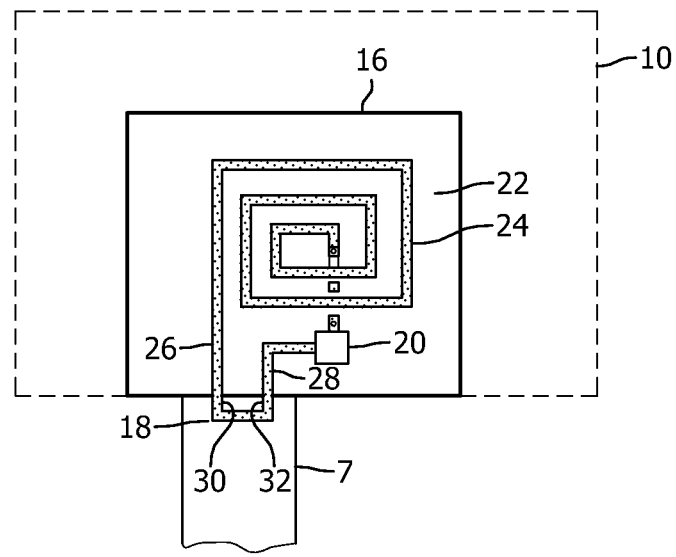
FIG. 2 is a schematic diagram showing the RFID component and coupling component of the system of FIG. 1 according to one particular embodiment.

FIG. 2 is a schematic diagram showing RFID component 16 and coupling component 18 according to one particular embodiment. In this embodiment, RFID component 16 includes a substrate 22 on which IC chip 20 is provided. In addition, an antenna element 24 is provided on substrate 22 and is operatively coupled to IC chip 20. Antenna element 24 is made of a suitable conductive material such as, without limitation, copper. Antenna element 24 includes first terminal portion 26 and second terminal portion 28. Coupling component 18 in this embodiment comprises a conductor element having a first terminal portion 30 and a second terminal portion 32. When fluid coupling device 10 is not coupled to delivery conduit 7, first and second terminal portions 26, 28 comprise an open circuit. As a result, in such a configuration, RFID component 16 is not functional since the antenna element 24 includes the open circuit. However, when fluid coupling device 10 is coupled to delivery conduit 7, first and second terminal portions 26, 28 are structured to electrically connected to first and second terminal portions 30, 32 as shown, thereby closing the circuit of antenna element 24 (essentially, coupling component 18 completes antenna element 24) and making RFID component 16 functional.

Figure 3:
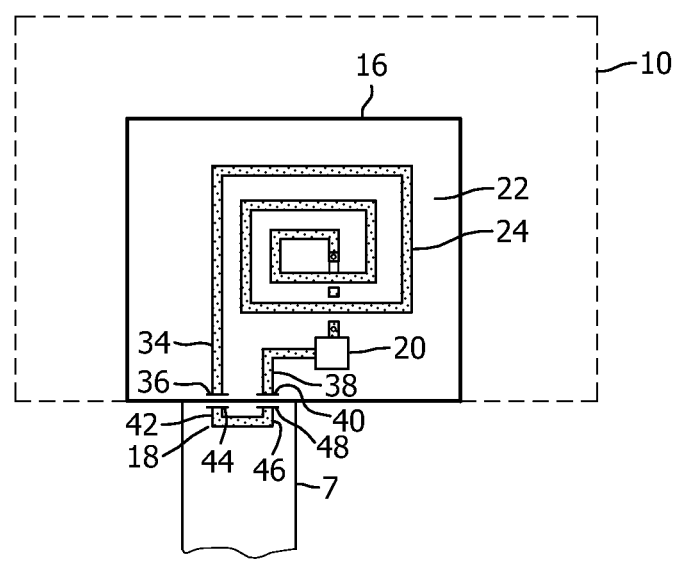
FIG. 3 is a schematic diagram showing the RFID component and coupling component of the system of FIG. 1 according to another particular embodiment

FIG. 3 is a schematic diagram showing RFID component 16 and coupling component 18 according to another particular embodiment. Like the embodiment shown in FIG. 2, in this embodiment RFID component 16 includes substrate 22 on which IC chip 20 is provided and antenna element 24. However, in this embodiment, antenna element 24 includes a first terminal portion 34 having an elongated terminal 36 and a second terminal portion 38 having an elongated terminal 40. Coupling component 18 in this embodiment comprises a conductor element having a first terminal portion 42 having an elongated terminal 44 and a second terminal portion 46 having an elongated terminal 48. When fluid coupling device 10 is not coupled to delivery conduit 7, first and second terminal portions 34, 38 comprise an open circuit. As a result, in such a configuration, RFID component 16 is not functional since the antenna element 24 includes the open circuit. However, when fluid coupling device 10 is coupled to delivery conduit 7, elongated terminals 36 and 40 are structured to be capacitively coupled to elongated terminals 44 and 48, respectively, as shown. At high frequencies, the capacitive coupling between elongated terminals 36 and 40 and elongated terminals 44 and 48 acts like a conductor, thereby closing the circuit of antenna element 24 (essentially, coupling component 18 completes antenna element 24) and making RFID component 16 functional. One advantage of the embodiment of FIG. 3 is that elongated terminals 36 and 40 and elongated terminals 44 and 48 can be embedded within fluid coupling device 10 and delivery conduit 7, respectively, so as to avoid having exposed contacts as is the case in the embodiment of FIG. 2.

Figure 4:
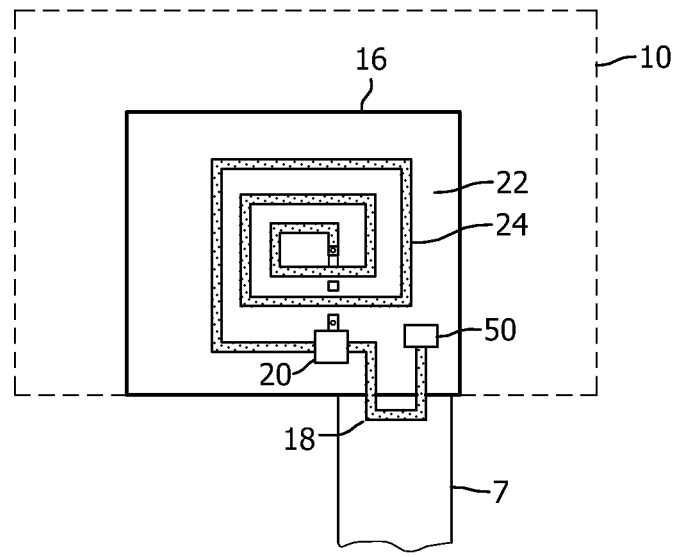
FIGS. 4 and 5 are schematic diagrams showing the RFID component and coupling component of the system of FIG. 1 according to other particular embodiments.

FIG. 4 is a schematic diagram showing RFID component 16 and coupling component 18 according to another particular embodiment. Like the embodiments shown in FIGS. 2 and 3, in this embodiment RFID component 16 includes substrate 22 on which IC chip 20 is provided and antenna element 24 forming a complete antenna. However, in this embodiment RFID component 16 and coupling component 18 together operate as an active RFID tag. Thus, a battery 50 (or another suitable power supply such as a supercapacitor) is provided on substrate 22. Battery 50, however, only becomes operatively coupled to IC chip 20 when fluid coupling device 10 is coupled to delivery conduit 7. In such a condition (shown in FIG. 4), coupling component 18 completes the circuit between battery 50 and IC chip 20. Thus, when fluid coupling device 10 is not coupled to delivery conduit 7, RFID component 16 is not functional because IC chip 20 is not powered. However, when fluid coupling device 10 is coupled to delivery conduit 7, RFID component 16 is functional because IC 20 receives power from battery 50.

Figure 5:
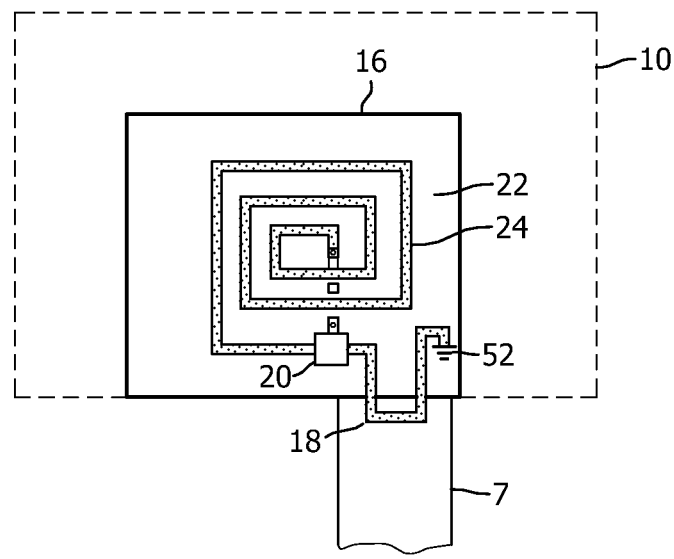

FIG. 5 is a schematic diagram showing RFID component 16 and coupling component 18 according to still another particular embodiment. Like the embodiments shown in FIG. 4, in this embodiment RFID component 16 includes substrate 22 on which IC chip 20 is provided and antenna element 24 forming a complete antenna. However, in this embodiment, IC chip 20 has an enable PIN that must be tied to a ground 52 in order for IC chip to be functional. When fluid coupling device 10 is not coupled to delivery conduit 7, there is an open circuit between the enable PIN and ground 52. As a result, RFID component 16 is not functional. However, when fluid coupling device 10 is coupled to delivery conduit 7, coupling component 18 electrically connects the enable PIN of IC chip 20 to ground 52, thereby providing an enabling signal to the enable PIN and making RFID component 16 functional.

The embodiments shown in FIGS. 2-5 are meant to be exemplary, and it should be understood that other mechanisms for making RFID component 16 fully functional when it is coupled to delivery conduit 7 are possible within the scope of the present invention.

Figure 6:
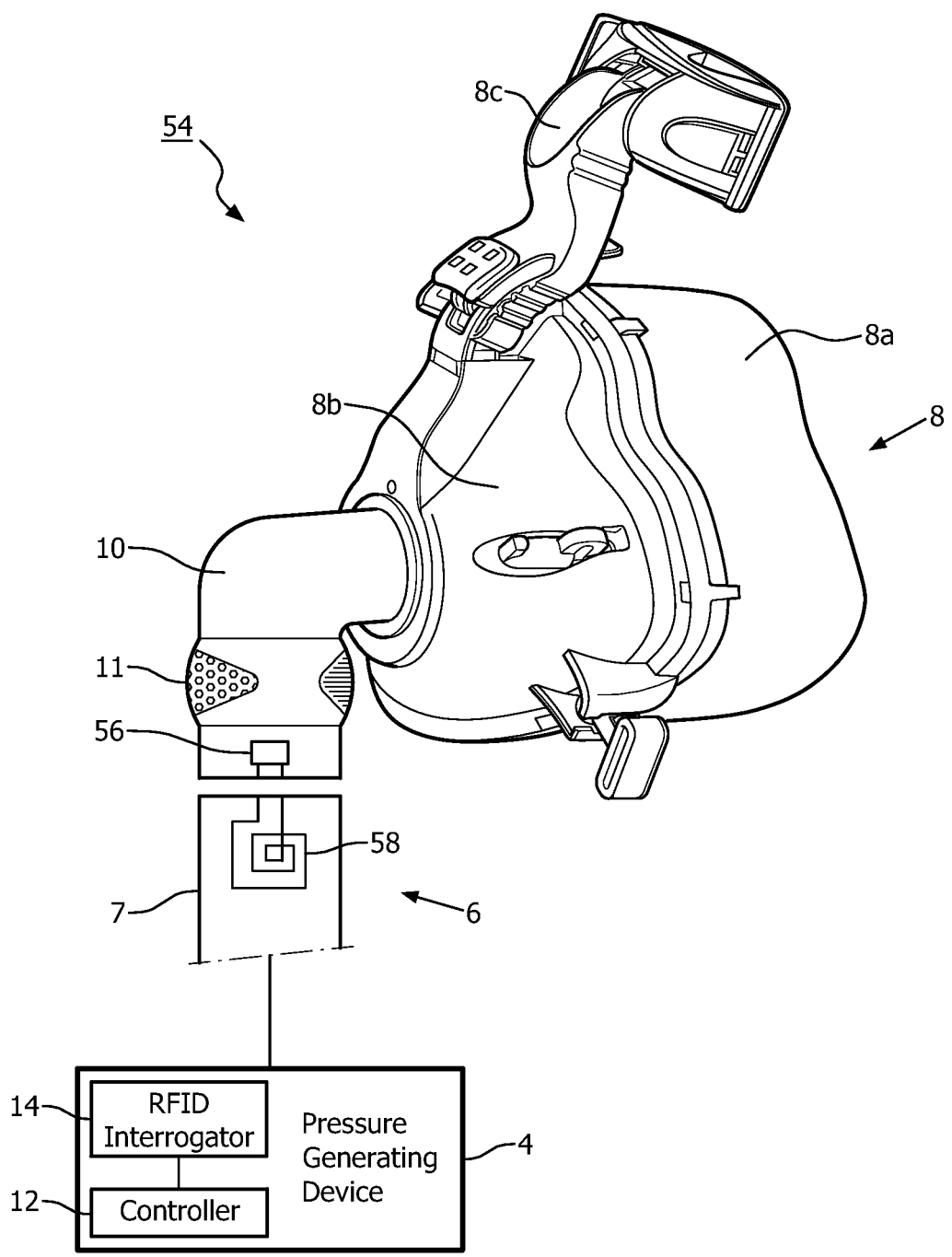
FIGS. 6, 7, 8, and 9 are schematic diagrams of airway pressure support systems adapted to provide a regimen of respiratory therapy to a patient according to an alternative embodiments.

A pressure support system 54 adapted to provide a regimen of respiratory therapy to a patient according to an alternative embodiment is generally shown in FIG. 6. System 54 includes many of the same components as airway pressure support system 2 shown in FIG. 1, and those components are labeled with like reference numerals in FIG. 6. In addition, as seen in FIG. 6, fluid coupling device 10 is provided with and supports an IC chip 56, which is similar to IC chip 20, and the second end of delivery conduit 7 is provided with and supports an RF antenna 58. IC chip 56 stores information that identifies patient interface device 8 to pressure generating device 4 (.e.g., by type or style), and may include further information that provides one or more operating parameters for pressure generating device 4 to be associated with patient interface device 8.

According to an aspect of the present embodiment, IC chip 56 is structured so that it is not fully functional, meaning it is not enable to communicate with RFID interrogator 14 (e.g. when polled by RFID interrogator 14) unless and until patient interface device 8 is coupled to delivery conduit 7. More specifically, fluid coupling device 10, IC chip 56, delivery conduit 7 and RF antenna 58 are structured so that when patient interface device 8 is coupled to delivery conduit 7, IC chip 56 will be operatively coupled to RF antenna 58 and IC chip 56 and RF antenna 58 will together form a complete RFID tag. Thereafter, RFID interrogator 14 may send an RF interrogation/polling signal to IC chip 56 which will cause IC chip 56 to transmit via RF the information stored therein. As a result, pressure generating device 4 will be able to identify patient interface device 8 and control operation based on the information that is received. In addition, as will be appreciated, any other similarly structured patient interface devices 8 that may be within range of RFID interrogator 14 (e.g., in the same room) will have IC chips 56 that are not fully functional because the patient interface device 8 is not coupled to delivery conduit 7.

Figure 7:
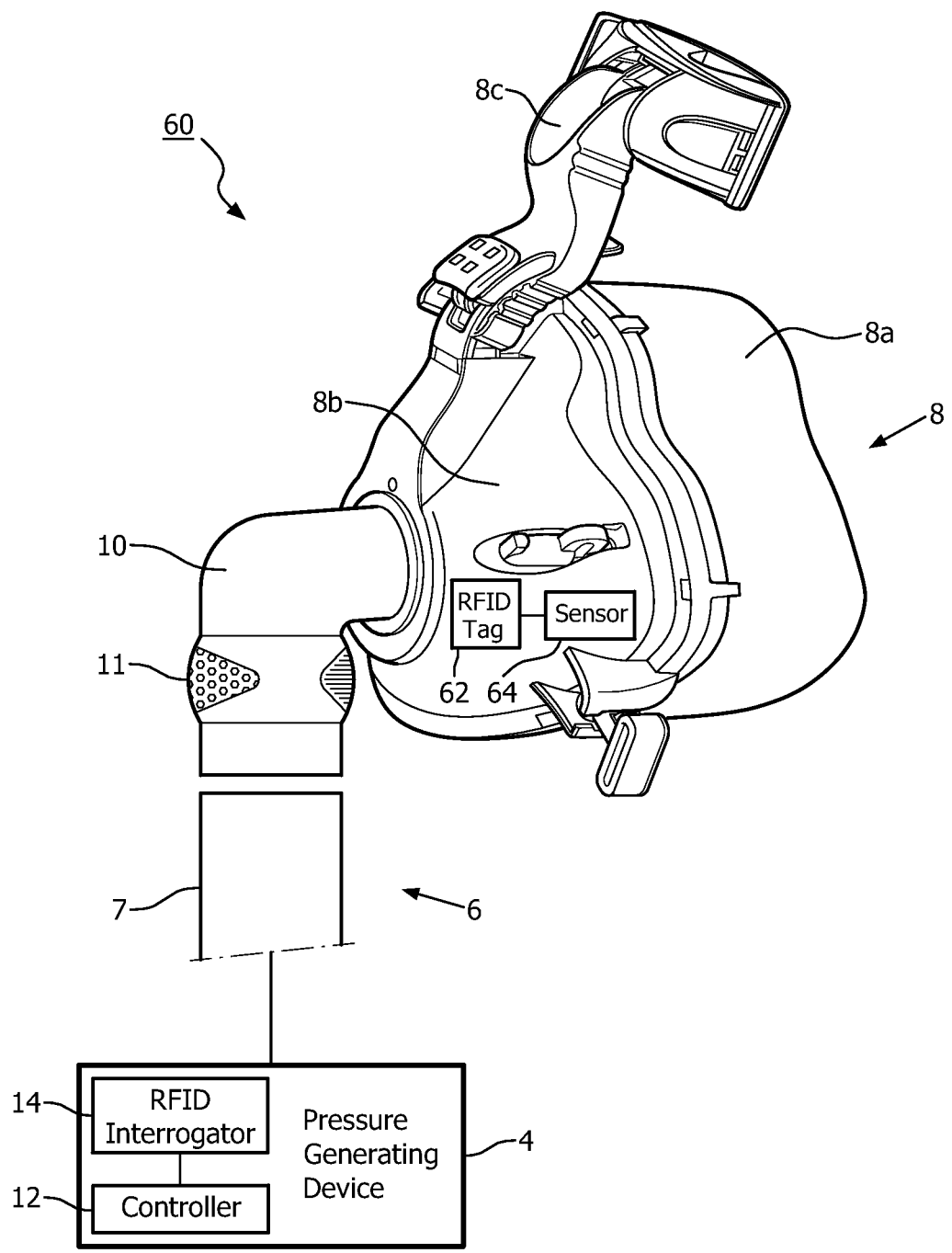

A pressure support system 60 adapted to provide a regimen of respiratory therapy to a patient according to a further alternative embodiment is generally shown in FIG. 7. System 60 includes many of the same components as airway pressure support system 2 shown in FIG. 1, and those components are labeled with like reference numerals in FIG. 7. In addition, as seen in FIG. 7, shell 8b is provided with and supports an RFID tag 62 and a sensor 64. RFID tag 62 may be a passive tag or an active tag and includes an IC chip similar to IC chips 20 and 56 described elsewhere herein and an RF antenna. In addition, sensor 64 is operatively coupled to the IC chip of RFID tag 62 and provides information about the parameter or parameters it senses to the IC chip of RFID tag 62.

In the present embodiment, sensor senses various parameters which may indicate that patient interface device 8 is coupled to pressure generating device 4 and is being used by a patient. For example, and without limitation, sensor 64 may be a pressure sensor that senses the pressure within patient interface device 8, a temperature sensor that senses the temperature within patient interface device 8 or a humidity sensor that senses the humidity level within patient interface device 8. In this embodiment, the IC chip of RFID tag 62 is programmed to monitor the parameter information it receives from sensor 64 and only enable RF communications when the parameter information indicates that patient interface device 8 is coupled to pressure generating device 4 and is being used by a patient. For example, in the case where sensor 64 is a pressure sensor, the IC chip of RFID tag 62 may be programmed to monitor the sensed pressure and enable RF communications only when the sensed pressure reaches or exceeds a level that indicates that patient interface device 8 is actually being used. Similarly, in the case where sensor 64 is a temperature sensor or a humidity sensor, the IC chip of RFID tag 62 may be programmed to monitor the sensed temperature or humidity level and enable RF communications only when the sensed temperature or humidity level reaches or exceeds a level that indicates that patient interface device 8 is actually being used.

Figure 8:
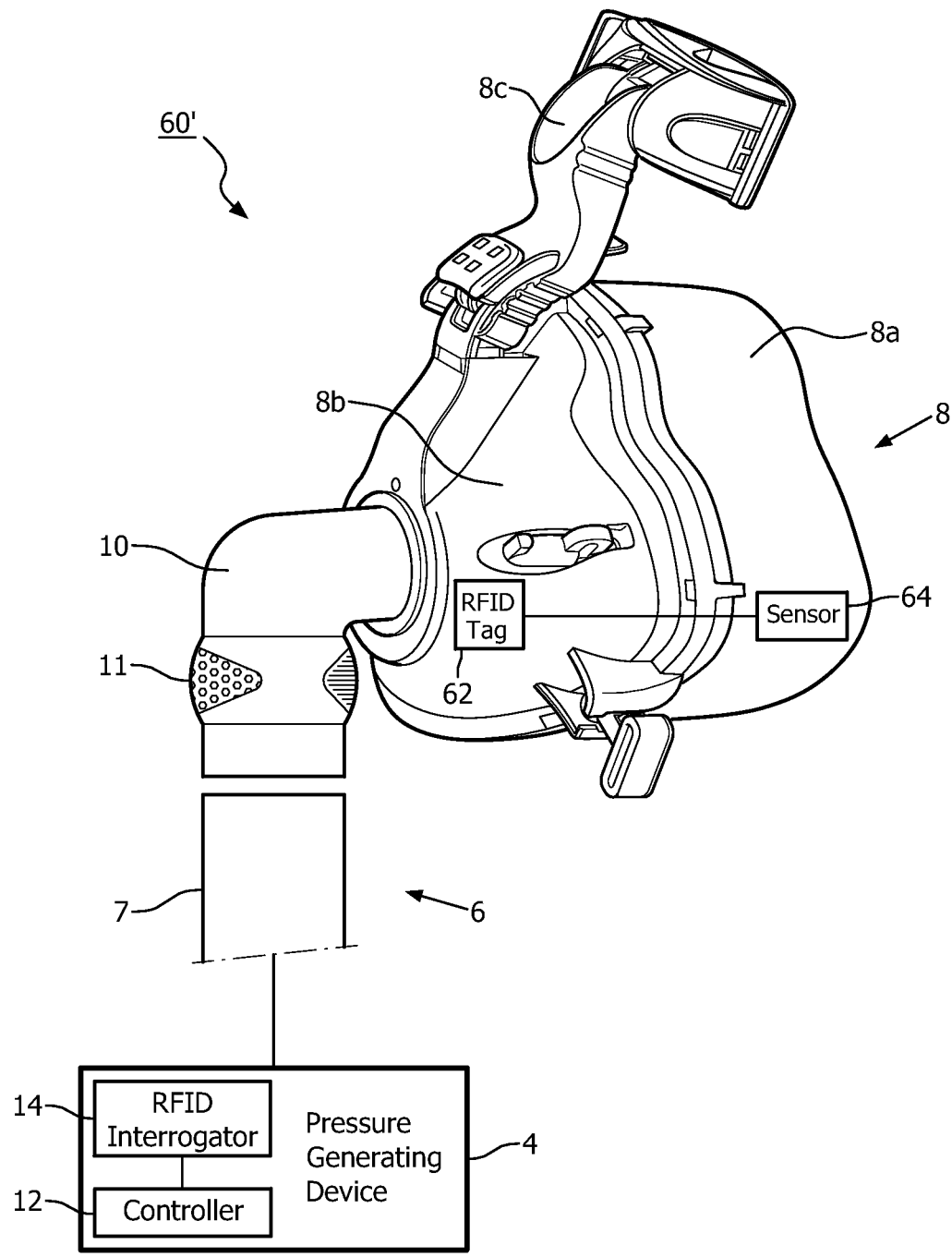

In a further alternative embodiment, shown in FIG. 8 and labeled 60', sensor 64 may be a conductivity sensor provided on cushion 8a that is able to detect when cushion 8a is in contact with a patient's face. In this embodiment, the IC chip of RFID tag 62 (which may be provided on shell 8b, cushion 8a, or elsewhere) is programmed to monitor the output of sensor 64 and enable RF communications only when the output indicates that patient interface device 8 is being worn.

Figure 9:
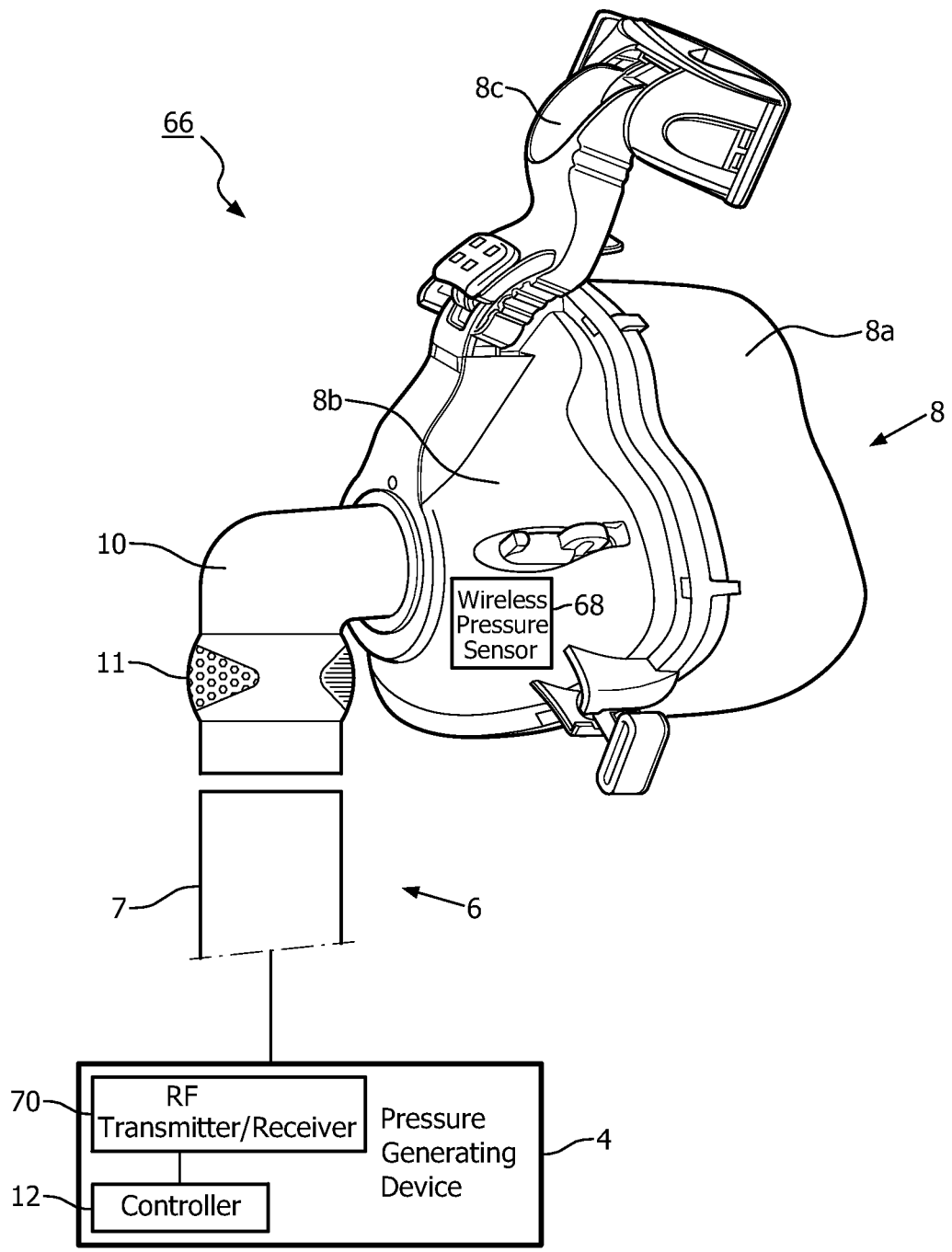

A pressure support system 66 adapted to provide a regimen of respiratory therapy to a patient according to a further alternative embodiment is generally shown in FIG. 9. System 66 includes many of the same components as airway pressure support system 2 shown in FIG. 1, and those components are labeled with like reference numerals in FIG. 9. In addition, as seen in FIG. 9, shell 8b is provided with and supports wireless pressure sensor 68. Wireless pressure sensor 68 is a device that will electrically resonate (emit RF) at a particular frequency when excited by RF energy of the particular (resonant) frequency. In addition, wireless pressure sensor 68 is structured such that the particular resonant frequency at which wireless pressure sensor 68 will resonate varies in response to pressure changes that it is subjected to.

In one exemplary embodiment, wireless pressure sensor 68 comprises an elastomeric diaphragm (made of, for example, silicone rubber or a thermoplastic elastomer) that has a wire filament (made of a conductive metal such as copper) embedded therein (or provided on the outer surface thereof) wherein the size and shape of the filament determines the resonant frequency. In addition, the elastomeric diaphragm has axisymmetric shape like a dome (or any oblong or elliptical shape that would deform in a non-repeatable manner) and will deflect in response to pressure changes. That deflection deforms the filament and as a result changes the resonant frequency. Wireless pressure sensor 68 may also take the form of the sensor described in U.S. Pat. No. 6,111,520 or the sensor described in United States Patent Application Publication No. 2006/0117859, the disclosures of which are incorporated herein by reference. It should be understood that these examples are not meant to be limiting, and that other configurations and structures for wireless pressure sensor 68 may also be used within the scope of the present invention.

Thus, the resonant frequency of wireless pressure sensor 68 at any particular time can be correlated to the pressure that is currently affecting wireless pressure sensor 68 and can therefore be used to measure the pressure inside patient interface device 8. To do so, wireless pressure sensor 68 can be designed so that there are a possible range of resonant frequencies depending on the current pressure. To determine the pressure at any given time, RF transmitter/receiver 70 provided in pressure generating device 4 can emit RF energy across the possible range of resonant frequencies. When wireless pressure sensor 68 resonates and emits an RF signal back, the specific resonant frequency that is received RF transmitter/receiver 70 can then be correlated to an associated pressure value in controller 12.

Figure 10:
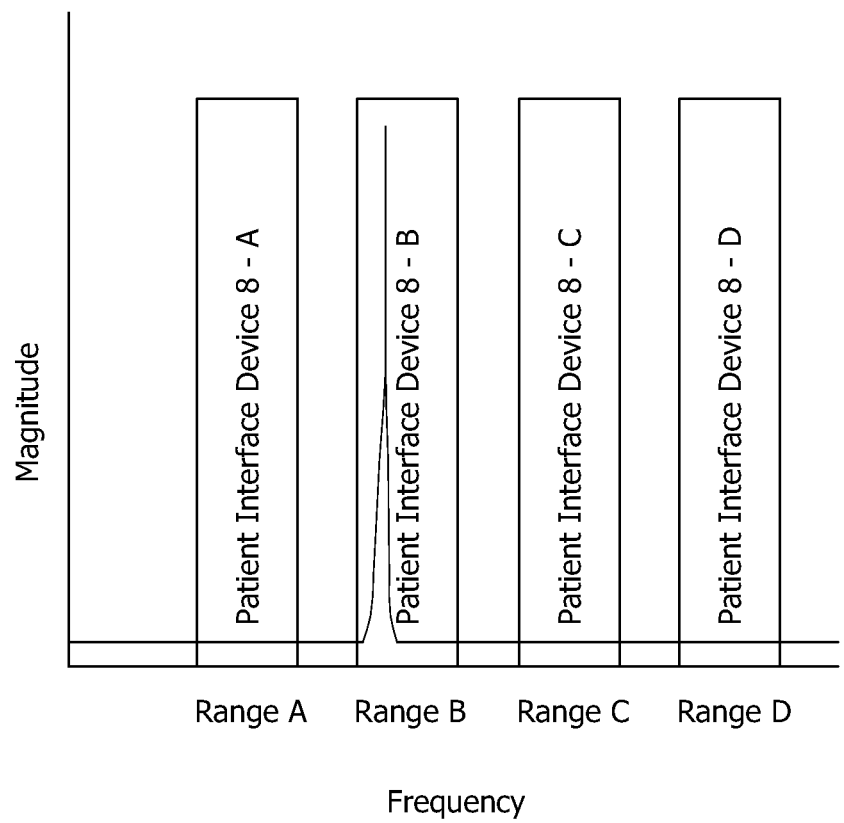
FIG. 10 is a plot showing resonant frequency ranges for four different patient interface devices that may be employed in the embodiment of FIG. 9.

In addition, according to one particular embodiment and aspect of the invention, wireless pressure sensors 68 provided in a number of patient interface devices 8 may be used to uniquely identify the particular patient interface devices 8. Specifically, a number of different wireless pressure sensors 68 can be designed such that each one has a different, non-overlapping possible range of resonant frequencies. For example, patient interface device 8-A could have wireless pressure sensor 68-A having resonant range A, patient interface device 8-B could have wireless pressure sensor 68-B having resonant range B, patient interface device 8-C could have wireless pressure sensor 68-C having resonant range C, and patient interface device 8-D could have wireless pressure sensor 68-D having resonant range D as illustrated in FIG. 10.

In operation, when one of the patient interface devices 8 is operatively coupled to pressure generating device 4 for use, RF transmitter/receiver 70 will emit RF energy across all of the possible range of resonant frequencies (range A, range B, range C and range D). When the wireless pressure sensor 68 in the particular patient interface device 8 being used resonates and emits an RF signal back (see the example shown in FIG. 10), the specific resonant frequency that is received at RF transmitter/receiver 70 can be supplied to controller 12 and used to identify the particular patient interface device 8 and determine pressure. In particular, it will first be determined which range (A-D) the received RF resonant frequency falls within. Based on that, the specific wireless pressure sensor 68 (A-D) and thus the particular patient interface device 8 (A-D) can be identified. Also, the specific resonant frequency that is received may then be correlated to an associated pressure value.

Moreover, according to one particular embodiment, in connection with each of the resonant ranges A-D, an initial threshold portion of the resonant range (from the beginning of the range to a specified point within the range) and a remaining portion of the resonant range (from the specified point within the range to the end of the range) are defined, wherein measured pressures corresponding to the initial threshold portion indicate that the patient interface device is not yet in use and measured pressures corresponding to the remaining portion indicate that the patient interface device is in use. In this embodiment, controller 12 is programmed such that it will not identify and recognize the particular patient interface device 8 unless it is determined that the specific resonant frequency that is received is above the initial threshold portion and thus within the remaining portion of the resonant range A-D in question. Thus, in this embodiment, wireless identification of a patient interface device 8 is enabled only if it is determined that the patient interface device 8 is operatively coupled to pressure generating system 4 and in use.

Figure 11:
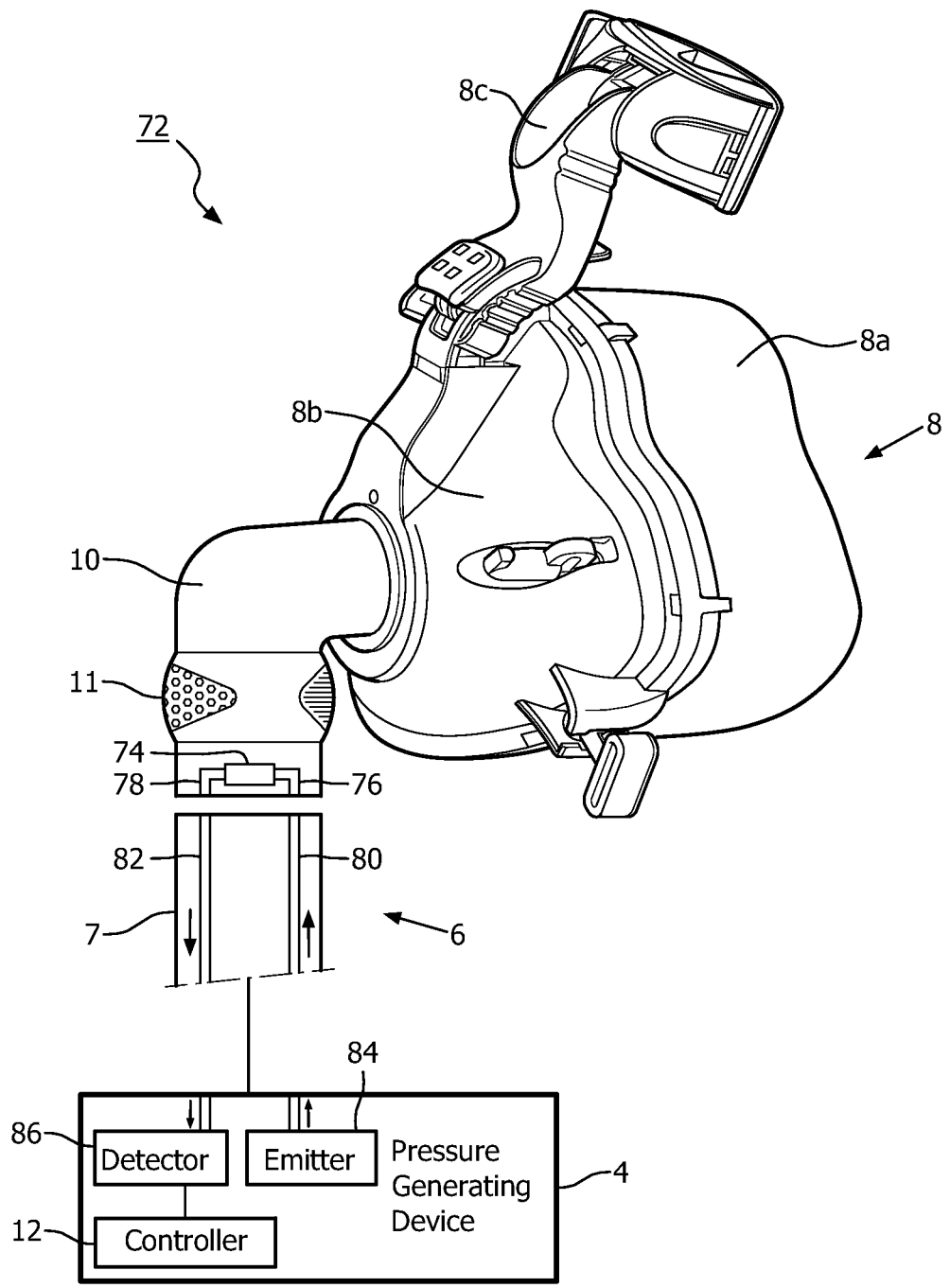
FIG. 11 is a schematic diagram of a pressure support system adapted to provide a regimen of respiratory therapy to a patient according to a further alternative embodiment.

A pressure support system 72 adapted to provide a regimen of respiratory therapy to a patient according to a further alternative embodiment is generally shown in FIG. 11. System 72 includes many of the same components as airway pressure support system 2 shown in FIG. 1, and those components are labeled with like reference numerals in FIG. 11. In addition, as seen in FIG. 11, fluid coupling device 10 of patient interface device 8 is provided with and supports an optical filter 74, a fiber optic pipe 76, and a fiber optic pipe 78.

Fiber optic pipe 76 is coupled to an input of optical filter 74, and fiber optic pipe 78 is coupled to an output of optical filter 74. Optical filter 74 is structured to receive as an input broadband light and output light of a specific frequency or range of frequencies that is associated with the patient interface device 8. Also, according to this embodiment, a number of patient interface devices 8 are provided, each one having an optical filter 74 that outputs different specific frequency or range of frequencies unique to that patient interface device 8. Thus, as described below, the specific frequency or range of frequencies associated with each of the patient interface devices 8 may be used to identify the patient interface devices 8.

Furthermore, delivery conduit 7 is provided with and supports a fiber optic pipe 80 and a fiber optic pipe 82 along the entire length thereof. A first end of fiber optic pipe 80 is operatively coupled to an optical emitter 84, which is structured to emit broadband light of a particular frequency band. A first end of fiber optic pipe 82 is operatively coupled to optical detector 86. In addition, when fluid coupling device 10 is coupled to delivery conduit 7, the second end of fiber optic pipe 80 becomes operatively coupled to fiber optic pipe 76, and the second end of fiber optic pipe 82 becomes operatively coupled to fiber optic pipe 78. As a result, a complete optical circuit from optical emitter 84 to optical detector 86 through optical filter 74 is created.

In operation, when fluid coupling device 10 is coupled to delivery conduit 7, optical emitter 84 is caused to emit broadband light. That light is transmitted through fiber optic pipes 80 and 76 to optical filter 74. Optical filter 74 filters the receives light and outputs filtered light consisting of either a single frequency or range of frequencies that is a subset of the frequencies of the broadband light. The filtered light is then transmitted through fiber optic pipes 78 and 82 to optical detector 86. Optical detector 86 is structured to be able to determine the particular frequency or range of frequencies that is received. That information is passed to controller 12, which may then use it to identify the patient interface device 8 and control operation of pressure generating device 4 based on the identification.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. In addition, while the invention has been described herein in connection with the identification of a patient interface device, it will be understood that the invention may be employed to wirelessly identify other components, such as, without limitation, hoses, humidifiers, filters, etc., when they are coupled to the pressure generating device so that operation of the pressure generating device can be automatically adjusted.

What is claimed is:

1. A pressure support system, comprising:
   a pressure generating device structured to produce a flow of gas, wherein the pressure generating device includes an RFID interrogating device;
   a delivery conduit coupled to the pressure generating device such that the pressure generating device is structured to deliver the flow of gas to the delivery conduit, the delivery conduit including a coupling component;

a component structured to be selectively coupled to the delivery conduit, wherein the component includes an RFID chip, an antenna element operatively coupled to the RFID chip, and an open circuit portion operatively coupled to the RFID chip and the antenna element, wherein the RFID chip is unable to perform wireless communications through the antenna element when the open circuit portion is not closed, and wherein the coupling component closes the open circuit portion responsive to the component being coupled to the delivery conduit to enable the RFID chip to wirelessly communicate with the RFID interrogating device through the antenna element such that the component is able to be wirelessly identified by the pressure generating device.

2. The pressure support system according to claim 1, wherein the component is further structured to wirelessly communicate identification information to the pressure generating device only when the component is coupled to the pressure generating device.

3. The pressure support system according to claim 1, wherein the component is a patient interface device.

4. The support system according to claim 3, wherein the antenna element includes the open circuit portion, wherein the coupling component comprises a conductor, and wherein the conductor contacts and closes the open circuit portion when the patient interface device is operatively coupled to the delivery conduit.

5. The pressure support system according to claim 3, wherein the antenna element includes the open circuit portion, wherein the coupling component comprises a conductor, and wherein the conductor forms a capacitive connection with the open circuit portion and closes the open circuit portion when the patient interface device is operatively coupled to the delivery conduit.

6. The pressure support system according to claim 3, wherein the patient interface device includes a power supply coupled to the open circuit portion, wherein the coupling component comprises a conductor, wherein the conductor contacts and closes the open circuit portion and thereby operatively couples the power supply to the RFID chip when the patient interface device is operatively coupled to the delivery conduit, and wherein the power supply is coupled to the RFID chip only when the patient interface device is operatively coupled to the delivery conduit.

7. The pressure support system according to claim 3, wherein the RFID chip has an enabling input coupled to the open circuit portion, wherein the RFID chip is structured to be able to perform wireless communications only when an enabling signal is provided to the enabling input, wherein the coupling component comprises a conductor, and wherein the conductor contacts and closes the open circuit portion and thereby causes an enabling signal to be provided to the enabling input through the conductor when the patient interface device is operatively coupled to the delivery conduit.

8. A pressure support system, comprising:
a pressure generating device structured to produce a flow of gas, wherein the pressure generating device includes an RFID interrogating device; and
a patient interface device structured to be selectively coupled to the pressure generating device, wherein the patient interface device includes an RFID tag and a sensor operatively coupled to the RFID tag, wherein the pressure generating device and the patient interface device are structured to enable the patient interface device to be wirelessly identified by the pressure generating device only when patient interface device is coupled to the pressure generating device, wherein the sensor is structured to sense a parameter indicating a condition within the patient interface device, and wherein wireless communication by the RFID tag with the RFID interrogating device is enabled only when the sensed parameter indicates that the patient interface device is coupled to the pressure generating device and is being used by a patient.

9. The pressure support system according to claim 8, wherein the sensor is selected from the group consisting of a pressure sensor that senses a pressure within the patient interface device, a temperature sensor that senses a temperature within the patient interface device, and a humidity sensor that senses a humidity level within patient interface device.

10. A pressure support system, comprising:
a pressure generating device structured to produce a flow of gas, wherein the pressure generating device includes an RFID interrogating device: and
a patient interface device structured to be selectively coupled to the pressure generating device, wherein the patient interface device includes an RFID tag and a sensor operatively coupled to the RFID tag, the sensor being structured to sense a parameter indicating that the patient interface device is in contact with a patient's face, wherein the pressure generating device and the patient interface device are structured to enable the patient interface device to be to wirelessly identified by the pressure generating device only when patient interface device is coupled to the pressure generating device, and wherein wireless communication by the RFID tag with the RFID interrogating device is enabled only when the sensor senses the parameter indicating that the patient interface device in contact with the patient's face.

11. The pressure support system according to claim 10, wherein the sensor is a conductivity sensor provided on a cushion of the patient interface device that is able to detect when the cushion is in contact with a patient's face.

12. A pressure support system, comprising:
a pressure generating device structured to produce a flow of gas, wherein the pressure generating device includes an RF transmitter/receiver module operatively coupled to a controller:
a patient interface device structured to be selectively coupled to the pressure generating device, wherein the patient interface device includes a wireless pressure sensor that is structured to resonate at any one of a plurality of resonant frequencies within a first range of frequencies based on a pressure to which the wireless pressure sensor is subjected, the particular one of the plurality of resonant frequencies being determined by a current pressure within the patient interface device, wherein the RF transmitter/receiver module is structured to emit RF energy across a second range of frequencies and receive RF energy emitted by the wireless pressure sensor in response to the RF energy across the second range of frequencies, wherein the controller is programmed to receive the RF energy emitted by the wireless pressure sensor and identify the patient interface device only if a frequency of the RF energy emitted by the wireless pressure sensor is determined to be within a predetermined subset of the first range of frequencies, the predetermined subset of the first range of frequencies corresponding to pressures within the patient interface device that indicate that the patient interface device is being used by a patient.

13. A method of identifying a component in an airway pressure support system, comprising:

coupling the component to a delivery conduit coupled to a pressure generating device of the airway pressure support system in a manner such that the pressure generating device is structured to deliver a flow of gas to the delivery conduit, wherein the delivery conduit includes a coupling component, the pressure generating device includes an RFID interrogating device, and the component includes an RFID chip, an antenna element operatively coupled to the RFID chip, and an open circuit portion operatively coupled to the RFID chip and the antenna element, wherein the RFID chip is unable to perform wireless communications through the antenna element when the open circuit portion is not closed; and responsive to the component being coupled to the delivery conduit, closing the open circuit portion using the coupling component and thereby enabling the RFID chip to wirelessly communicate with the RFID interrogating device through the antenna element such that the component is able to be to wirelessly identified by the pressure generating device.

14. The method according to claim 13, wherein the enabling comprises enabling the component to wirelessly communicate identification information to the pressure generating device only when the component is coupled to the pressure generating device.

15. The method according to claim 13, wherein the component is a patient interface device.

16. The method according to claim 15, wherein the antenna element includes the open circuit portion.

17. The method according to claim 15, wherein the closing the open circuit portion causes power to be provided to the RFID chip from a power supply included as part of the patient interface device and coupled to the open circuit portion.

18. The method according to claim 15, wherein the RFID chip has an enabling input coupled to the open circuit portion, wherein the RFID chip is structured to be able to perform wireless communications only when an enabling signal is provided to the enabling input, and wherein the closing the open circuit portion causes an enabling signal to be provided to the enabling input through the coupling component.

19. A method of identifying a patient interface device in an airway pressure support system, comprising:
coupling the patient interface device to a pressure generating device of the airway pressure support system in a manner such that the pressure generating device is structured to deliver a flow of gas to the patient interface device, wherein the patient interface device includes an RFID tag, wherein the pressure generating device includes an RFID interrogating device, and wherein the pressure generating device and the patient interface device are structured to enable the patient interface device to be wirelessly identified by the pressure generating device only when patient interface device is coupled to the pressure generating device: and
sensing a parameter indicating a condition within the patient interface device and enabling the RFID tag to wirelessly communicate with the RFID interrogating device only when the sensed parameter indicates that the patient interface device is coupled to the pressure generating device and is being used by a patient.

20. A method of identifying a patient interface device in an airway pressure support system, comprising:
coupling the patient interface device to a pressure generating device of the airway pressure support system in a manner such that the pressure generating device is structured to deliver a flow of gas to the patient interface device, wherein the patient interface device includes an RFID tag, wherein the pressure generating device includes an RFID interrogating device, and wherein the pressure generating device and the patient interface device are structured to enable the patient interface device to be wirelessly identified by the pressure generating device only when patient interface device is coupled to the pressure generating device: and
sensing whether the patient interface device is in contact with a patient's face and enabling the RFID tag to wirelessly communicate with the RFID interrogating device only when it is sensed that the patient interface device in contact with the patient's face.

21. A method of identifying a patient interface device in an airway pressure support system, comprising:
coupling the patient interface device to a pressure generating device of the airway pressure support system in a manner such that the pressure generating device is structured to deliver a flow of gas to the patient interface device, wherein the patient interface device includes a wireless pressure sensor that is structured to resonate at any one of a plurality of resonant frequencies within a first range of frequencies based on a pressure to which the wireless pressure sensor is subjected, the particular one of the plurality of resonant frequencies being determined by a current pressure within the patient interface device;
emitting RF energy across a second range of frequencies;
receiving RF energy emitted by the wireless pressure sensor in response to the RF energy across the second range of frequencies; and
identifying the patient interface device only if a frequency of the RF energy emitted by the wireless pressure sensor is determined to be within a predetermined subset of the first range of frequencies, the predetermined subset of the first range of frequencies corresponding to pressures within the patient interface device that indicate that the patient interface device is being used by a patient.

22. A pressure support system, comprising:
a pressure generating device structured to produce a flow of gas, the pressure generating device having an optical emitter structured to emit broadband light and an optical detector;
a delivery conduit operatively coupled to the pressure generating device, the delivery conduit having a first light transmitting element operatively coupled to the optical emitter and a second light transmitting element operatively coupled to the optical detector;
a patient interface device structured to be selectively coupled to the delivery conduit, the patient interface device having an optical filter structured to be operatively coupled to the first light transmitting element and the second light transmitting element when the patient interface device is coupled to the delivery conduit, the optical filter being structured to receive the broadband light from the optical emitter through the first light transmitting element and in response thereto output filtered light of a specific frequency or range of frequencies that is associated with the patient interface device, wherein the filtered light is transmitted to the optical detector through the second light transmitting element, the optical detector being structured to detect the specific frequency or range of frequencies; and
a controller operatively coupled to the optical detector, the controller being programmed to identify the patient interface device based on the detected specific frequency or range of frequencies.

* * * * *